(12) United States Patent
Hashimoto (10) Patent No.: US 6,670,131 B2
(45) Date of Patent: Dec. 30, 2003

(54) NUCLEIC ACID DETECTION METHOD AND APPARATUS, AND VESSEL FOR DETECTING NUCLEIC ACID

(75) Inventor: Koji Hashimoto, Sagamihara (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 09/995,614

(22) Filed: Nov. 29, 2001

(65) Prior Publication Data

US 2002/0064795 A1 May 30, 2002

(30) Foreign Application Priority Data

Nov. 30, 2000 (JP) ........................... 2000-364614

(51) Int. Cl.[7] .................. C12Q 1/68; C12P 19/34; C12M 1/34; C07H 21/02; C07H 21/04
(52) U.S. Cl. .................. 435/6; 435/7.1; 435/91.1; 435/91.2; 435/287.2; 536/22.1; 536/23.1; 536/24.3; 536/24.31; 536/24.32; 536/24.33
(58) Field of Search ................. 435/6, 7.1, 91.1, 435/91.2, 287.2; 536/22.1, 23.1, 24.3–24.35

(56) References Cited

U.S. PATENT DOCUMENTS

| | | |
|---|---|---|
| 5,776,672 A | 7/1998 | Hashimoto et al. |
| 5,972,692 A | 10/1999 | Hashimoto et al. |
| 6,033,850 A | 3/2000 | Purvis |
| 6,365,400 B1 * | 4/2002 | Stanley ............... 435/285.2 |

FOREIGN PATENT DOCUMENTS

| | | |
|---|---|---|
| DE | 199 17 052 A1 | 10/2000 |
| EP | 0 478 319 A | 4/1992 |
| JP | 10 239240 A | 9/1998 |
| WO | WO 00 11473 A | 3/2000 |

OTHER PUBLICATIONS

Koji Hashimoto, et al. "Microfabricated Disposable DNA Sensor for Detection of Hepatitis B Virus DNA" Sensors and Actuators B vol. 46 1998, pp. 220–224.
Hashimoto K. et al., "Sequence–specific Gene Detection with a Gold Electrode Modified with DNA Probes and an Electrochemically Active Dye", Analytical Chemistry, vol. 66, No. 21, Nov. 1, 1994, pp. 3830–3833, XP–002242075.

* cited by examiner

Primary Examiner—Jeffrey Siew
(74) Attorney, Agent, or Firm—Oblon, Spivak, McClelland, Maier & Neustadt, P.C.

(57) ABSTRACT

There is disclosed a nucleic acid detection apparatus including a nucleic acid immobilized electrode constituted by immobilizing a nucleic acid probe to a conductor, a plurality of vessels for bringing the nucleic acid probe into contact with a subject substance, a counter electrode disposed on a bottom surface or a inside surface of the vessel, and an electric circuit for applying a voltage between the nucleic acid immobilized electrode and the counter electrode. A nucleic acid is detected by inserting the nucleic acid immobilized electrode into each vessel containing the subject substance, and using the counter electrode disposed on the bottom surface or inside surface of the vessel to electrically control reaction.

14 Claims, 9 Drawing Sheets

NUCLEIC ACID DETECTION METHOD AND APPARATUS, AND VESSEL FOR DETECTING NUCLEIC ACID

CROSS-REFERENCE TO RELATED APPLICATIONS

This application is based upon and claims the benefit of priority from the prior Japanese Patent Application No. 2000-364614, filed Nov. 30, 2000, the entire contents of which are incorporated herein by reference.

BACKGROUND OF THE INVENTION

1. Field of the Invention

The present invention relates to a nucleic acid detection method and apparatus for detecting presence/absence of a nucleic acid having a particular sequence in a subject substance, and a vessel for detecting the nucleic acid.

2. Description of the Related Art

In recent years, a gene detection technique by a nucleic acid immobilized array (DNA array) has attracted attention (Beattie et al. 1993, Fodor et al. 1991, Khrapko et al. 1989, Southern et al. 1994).

Figure 20:
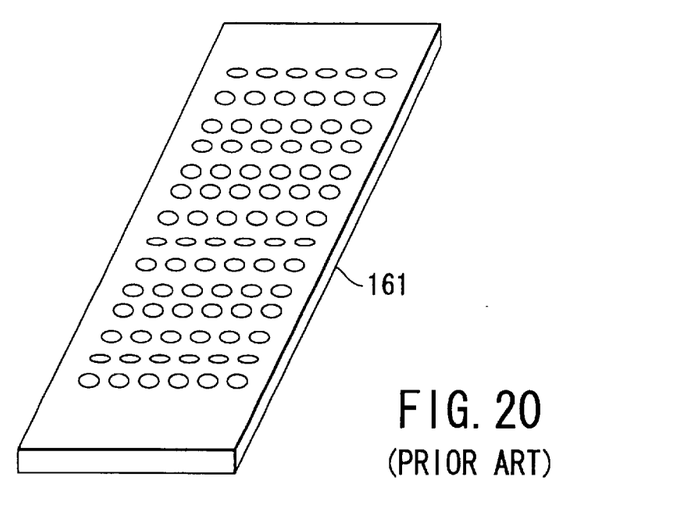
FIG. 20 is a perspective view showing a conventional DNA array.

For example, as shown in FIG. 20, the DNA array is constituted of a DNA array 161 of glass or silicon of several centimeters square in which $10^1$ to $10^5$ types of nucleic acid probes different from one another in sequence are immobilized. A subject gene labeled beforehand with fluorochrome, radioactive isotope (RI), or the like is reacted on the DNA array, or a mixture of an unlabeled subject gene and labeled oligonucleotide is reacted with sandwich hybridization. When a sequence complementary with the nucleic acid probe on the DNA array exists in the subject gene, a signal (fluorescent strength, RI strength) arising from a label is obtained in a particular site on the array. When the sequence and position of the immobilized nucleic acid probe are known beforehand, a base sequence present in the subject gene can easily be checked.

Since much information on the base sequence is obtained with a micro amount of samples, the DNA array is much expected not only as the gene detection technique but also as a sequence technique (Pease et al. 1994, Parinov et al. 1996).

Furthermore, a method of using a DNA array including an electrode formed by immobilizing the nucleic acid probe, and electrochemically controlling the hybridization reaction has also been reported (Heller et al. 1997). The nucleic acid has a minus charge in a phosphoric acid back bone. Therefore, when a plus voltage is applied to the electrode, the subject gene is concentrated on the electrode. With use of this method, the hybridization reaction, which has heretofore required several hours, ends only in several minutes.

However, a gene detection method using the DNA array is a method of using the fluorescence strength or the RI strength as an indication to detect hybrid formation of the nucleic acid probe and the subject gene on the DNA array. Therefore, an intricate and expensive pretreatment for labeling the subject gene with fluorochrome, RI, or the like beforehand is necessary. Moreover, since fluorescence or RI from a micro region has to be detected, a high-sensitivity fluorescence detection system having a high resolution is necessary. Accordingly, there is a problem that the system becomes complicated, large-sized, and expensive.

A further advanced gene detection technique based on an electrochemical method has also been reported (Hashimoto et al. 1994, Wang et al. 1998). This technique does not require the label of the subject gene. Moreover, for the detection, since the electric signal is measured, a complicated system such as fluorescence detection is unnecessary. In this technique, miniaturization of the system can be expected, and the technique can also be applied to the DNA array.

However, the known conventional DNA array is superior for the detection of varieties of genes with respect to one type of sample (subject substance). There is a problem that the array cannot necessarily be said to be suitable for treatment of varieties of samples.

Figure 21:
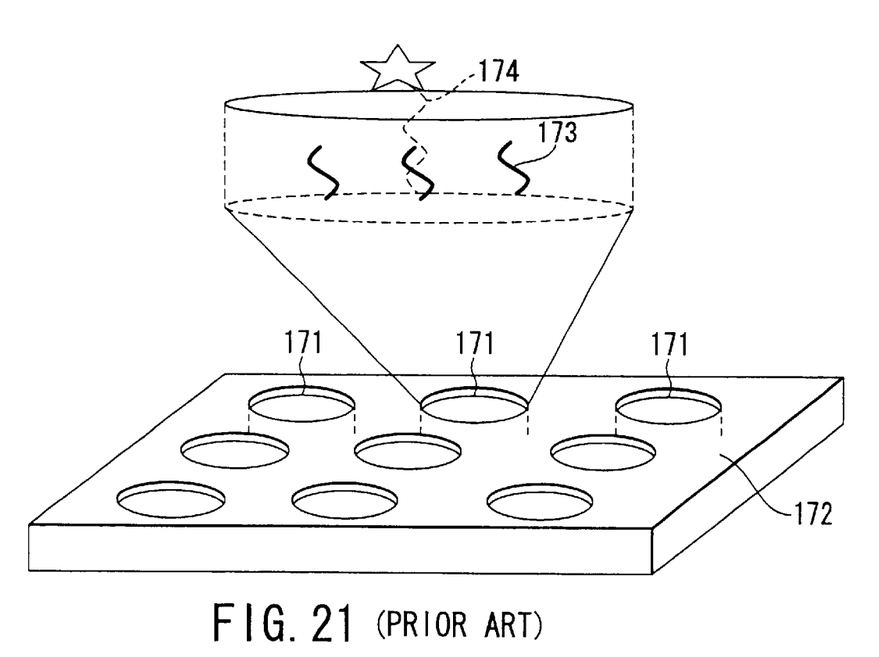
FIG. 21 is a schematic diagram showing a conventional gene detection method.

At present, a method in which a micro titer plate and an enzyme immunoassay are combined is used in detecting the genes of varieties of samples such as an infectious disease. FIG. 21 is a schematic diagram. A micro titer plate 172 including a plurality of bottomed vessels 171 is used so that different samples can separately be injected, and a nucleic acid probe 173 is disposed beforehand in each vessel 171.

Subsequently, the different samples including a subject gene 174 labeled beforehand with the fluorochrome, RI, or the like are individually injected into the respective vessels 171. When the sequence complementary with the nucleic acid probe exists in the subject gene, the signal arising from the label (fluorescence strength, RI strength) is obtained in the vessel. It is thus detected whether or not the subject gene of each sample is a gene having the particular sequence.

However, this method works excellently in the detection of many kinds of samples, but it entails such a problem that it is not very much suitable for detecting many kinds of genes. Further, in this method, the intricate and expensive pretreatment for labeling the subject gene with the fluorochrome, RI, or the like is necessary. Furthermore, since it is necessary to detect the fluorescence of the micro region, the high-sensitivity fluorescence detection system having a high resolution is necessary. Accordingly, there is a problem that the system becomes complicated, large, and expensive.

In a personalized medical treatment required in future, it is desired to easily detect the gene by a simple equipment even with respect to varieties of samples, and there is a demand for means which can perform the detection.

BRIEF SUMMARY OF THE INVENTION

An object of the present invention is to easily perform gene detection of many kinds of genes of many samples which has been difficult with a conventional gene detection technique with a simple equipment and at a high precision, and to precisely and efficiently perform gene examination expected in a tailor-made medical treatment, and the like.

In an embodiment of the present invention, an electrochemical method is used as a nucleic acid detection method. That is, a nucleic acid immobilized electrode constituted by immobilizing a nucleic acid probe onto a conductor, and a counter electrode are brought into contact with a subject substance. An electrochemical change between the nucleic acid immobilized electrode and the counter electrode attributed to hybridization reaction with the nucleic acid probe is detected in a nucleic acid in the subject substance, so that presence/absence of a particular nucleic acid in the subject substance is detected. Therefore, an intricate and expensive pretreatment for labeling the subject gene with fluorochrome, RI, and the like, or a high-sensitivity fluorescence detection system having a high resolution is unnecessary.

In another embodiment of the present invention, a plurality of vessels in which subject substances are contained are disposed, and a counter electrode is disposed on a bottom surface or an inside surface of the vessel. By a simple operation of injecting different subject substances into the respective vessels, inserting a nucleic acid immobilized electrode into each vessel, and bringing the electrode into contact with the subject substance, it is possible to separately detect an electrochemical change of each vessel. In this case, since the counter electrode is formed in the side surface or the bottom surface of each vessel beforehand, operability is enhanced and an apparatus constitution is simplified as compared with insertion of both the nucleic acid immobilized electrode and the counter electrode into each vessel.

Moreover, in another embodiment of the present invention, there is provided a method of electrochemically detecting presence of a nucleic acid having a particular sequence in a subject substance, comprising: preparing first and second vessels, wherein in the second vessel, a solution of a nucleic acid binding reagent is dispensed, and at least the second vessel has a counter electrode on a bottom surface or a inside surface thereof; inserting the subject substance into the first vessel; inserting a nucleic acid immobilized electrode having a conductor member and a nucleic acid probe immobilized on the conductor member, to the first vessel; making a hybridization reaction to occur in the first vessel; extracting the nucleic acid immobilized electrode from the first vessel and inserting it into the second vessel; and applying a predetermined voltage between the nucleic acid immobilized electrode and the counter electrode so as to measure an electrochemical signal of the nucleic acid binding reagent solution.

DETAILED DESCRIPTION OF THE INVENTION

Figure 1:
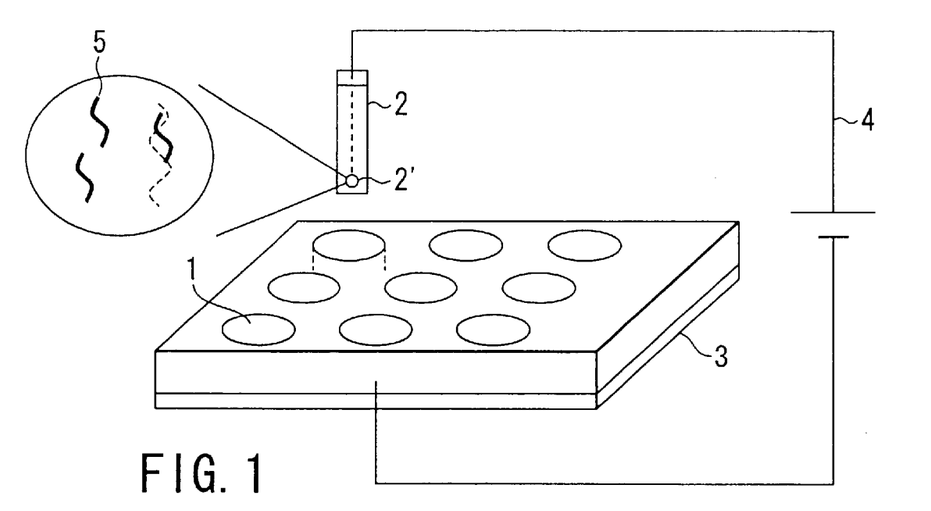
FIG. 1 is a block diagram showing a schematic constitution of a nucleic acid detection apparatus according to one embodiment of the present invention.

A constitution of a nucleic acid detection apparatus according to an embodiment of the present invention will be described with reference to a schematic diagram of FIG. 1. As shown in FIG. 1, the nucleic acid detection apparatus includes a nucleic acid immobilized electrode 2, a plurality of bottomed vessels 1 separated from one another, a counter electrode 3 disposed on a bottom surface or a side surface of the bottomed vessel 1, and an electric circuit 4 for applying a voltage between the nucleic acid immobilized electrode 2 and the counter electrode 3. The electric circuit 4 includes a control circuit for controlling application of the voltage, and a power source circuit connected to an external power source.

The nucleic acid immobilized electrode 2 may be constituted by forming a conductor in a substrate, or may be formed only of the conductor. Considering from strength, manufacturing cost, and the like, the conductor is preferably formed in the substrate. A nucleic acid probe 5 is immobilized in an exposed portion 2' of the conductor. A subject substance or a nucleic acid binding reagent is injected into each bottomed vessel 1.

The nucleic acid immobilized electrode 2 can be inserted into the bottomed vessel 1, and the nucleic acid probe 5 can contact the subject substance dispensed in the bottomed vessel 1.

When hybridization reaction of the target nucleic acid and nucleic acid probe occurs in the subject substance, an electrochemical change between the nucleic acid immobilized electrode and the counter electrode results from the reaction. Therefore, when the change is detected, presence/absence of the nucleic acid subjected to the hybridization reaction with the nucleic acid probe 5 in the subject substance can be detected.

As one of several embodiments of the nucleic acid detection apparatus, the apparatus has a two-electrodes system in which the nucleic acid immobilized electrode 2 is used as a working electrode, and only the working electrode and counter electrode 3 are used. As another embodiment, the apparatus has a three-electrodes system in which a reference electrode is used in addition to the working electrode and counter electrode. The reference electrode may be formed in the bottom surface or the side surface of the bottomed vessel 1 similarly as the counter electrode, or may be formed in the same substrate as that of the nucleic acid immobilized electrode 2.

A shape of the nucleic acid immobilized electrode is not particularly limited. For example, in the present embodiment, an outer shape of the electrode including a substrate portion is a columnar or cylindrical shape having a width not more than 6 mm and not less than 1 mm, so that the electrode can be inserted into a commercially available micro titer plate having 24, 48, 96, 384, or 1536 holes.

A plurality of nucleic acid immobilized electrodes may be disposed so that a plurality of subject substances can simultaneously be measured. Control of the plurality of nucleic acid immobilized electrodes may be realized by a matrix system employed in a liquid crystal display. Alternatively, the system may be an active matrix system in which a MOSFET is used. A MOS image sensor type scanning circuit can also be used.

The nucleic acid immobilized electrode 2 will be described hereinafter in more detail.

It is most preferable to use gold as a conductor 2' for immobilizing the nucleic acid probe 5 in the nucleic acid immobilized electrode 2 in which the nucleic acid probe 5 is immobilized. However, other materials can also be used. Examples of the material include an alloy of gold, single metals such as silver, platinum, mercury, nickel, palladium, silicon, germanium, gallium, and tungsten, an alloy of these metals, carbons such as graphite and glassy carbon, and an oxide or a compound of these components.

It is preferable to form the conductor on a substrate surface formed of other materials such as glass by plating, printing, sputtering, vapor deposition, and the like. With the vapor deposition, an electrode film can be formed by a resistance heating method, high-frequency heating method, and electron beam heating method. Moreover, for the sputtering, the electrode film can be formed by direct-current bipolar sputtering, bias sputtering, asymmetric alternating-current sputtering, getter sputtering, or high-frequency sputtering. Here, when gold is used in the conductor 2', an orientation index of (111) surface of a crystal structure of gold is important. The orientation index is obtained from the following equation by Willson's method.

Orientation index (hkl)=$IF_{(hkl)}/IFR_{(hkl)}$ hkl: surface index $IF_{(hkl)}$: relative strength of (hkl) surface $IFR_{(hkl)}$: $IF_{(hkl)}$ as standard gold described in an ASTM card The orientation index is particularly preferably 1 or more. Furthermore, the orientation index is preferably 2 or more. In order to enhance orientation properties, it is also effective to heat the substrate during the vapor deposition or the sputtering. A heating temperature is not particularly limited, but is preferably in a range of 50° C. to 500° C. Since the orientation properties are controlled, it is possible to uniformly control a nucleic acid probe 5 immobilized amount.

Moreover, with the vapor deposition or the sputtering of the conductor in the substrate, titanium, chromium, copper, or nickel, or an alloy of these metals is disposed alone or in combination as an adhesive layer between the substrate and gold, so that a stable electrode layer can be formed.

A material constituting the substrate in which the conductor 2' is formed in the nucleic acid immobilized electrode 2 is not particularly limited. It is possible to use, for example, inorganic insulating materials such as glass, quartz glass, silicon, alumina, sapphire, forsterite, silicon carbide, silicon oxide, and silicon nitride. Moreover, it is possible to use organic materials such as polyethylene, ethylene, polypropylene, polyisobutylene, polyethylene terephthalate, unsaturated polyester, fluoroplastic, polyvinyl chloride, polyvinylidene chloride, polyvinyl acetate, polyvinyl alcohol, polyvinyl acetal, acrylic resin, polyacrylonitrile, polystyrene, acetal resin, polycarbonate, polyamide, phenol resin, urea resin, epoxy resin, melamine resin, styrene-acrylonitrile copolymer, acrylonitrile-butadiene-styrene copolymer, silicone resin, polyphenylene oxide, and polysulfone.

When the conductor 2' having a desired shape is formed on the substrate in order to obtain the nucleic acid immobilized electrode 2, a photoresist material is preferably used to perform a photolithography process after forming the conductor on the substrate. Examples of the photoresist material include a photoresist for light exposure, photoresist for far ultraviolet radiation, photoresist for X rays, and photoresist for electron rays. For the photoresist for light exposure, examples of a main material include cyclized rubber, polycinnamic acid, and novolak resin. For the photoresist for far ultraviolet radiation, cyclized rubber, phenol resin, polymethyl isopropenyl ketone (PMIPK), polymethyl methacrylate (PMMA), and the like are used. Moreover, in addition to COP, and metal acrylate, various substances can be used in the resist for X rays. Furthermore, other substances such as PMMA can be used in the resist for electron rays.

A photoresist layer for use in performing photolithography is preferably not less than 100 angstroms and not more than 1 mm. The conductor is coated with the photoresist, the photoresist is patterned into a concave/convex pattern having a desired shape, and subsequently the patterned photoresist is used as a mask to etch the conductor, so that a conductor 2' area can be set to be constant. Thereby, the immobilized amount of the immobilized nucleic acid probe 5 becomes uniform among the respective electrodes, and measurement superior in reproducibility is enabled.

Moreover, the photoresist layer may be not only used as the mask for processing the conductor but also left as a protective film of the electrode.

Furthermore, when the photolithography process is used, the conductor can be prepared at a high precision, but a little more manufacturing cost is sometimes required. A printed substrate can also be used in order to prepare the electrode at a low cost. In this case, polyimide, glass epoxy resin, and the like can be used as the substrate material.

Subsequently, a method of immobilizing the nucleic acid probe 5 onto the conductor 2' of the nucleic acid immobilized electrode 2 will next be described. In order to immobilize the nucleic acid probe 5 in the conductor disposed in the nucleic acid immobilized electrode, first, a conductor surface is preferably activated. The conductor surface can be activated by potential sweeping in a solution of sulfuric acid. Moreover, mixed acid, aqua regia, and the like may also be used. Furthermore, the conductor surface can also be activated by treating the surface with a dry etching gas.

A single stranded nucleic acid whose base sequence is already known is used as the nucleic acid probe 5. A material constituting the nucleic acid probe 5 is not particularly limited, and it is possible to use DNA, RNA, PNA, nucleic acid of a methylphosphonate back bone, and other nucleic acid simulants.

A method of immobilizing the nucleic acid probe 5 is not particularly limited. For example, when coupling of gold and a thiol group introduced in the nucleic acid probe 5 is utilized, immobilization can easily be performed. Additionally, the immobilization is enabled by physical adsorption, chemical adsorption, hydrophobic coupling, embedding, shared coupling, and the like. Moreover, biotin-avidin coupling, and condensation agents such as carbodiimide can also be used. In this case, the immobilization can be facilitated by modifying the conductor surface with a molecule having an organoleptic group beforehand. Furthermore, in order to inhibit nonspecific adsorption of nucleic acid, nucleic acid binding reagents, and the like into the conductor surface, the conductor surface is preferably coated with mercaptan such as mercaptoethanol, or lipid such as stearyl amine.

When an immobilization apparatus called a DNA spotter or a DNA arrayer is used, the probe can relatively easily be immobilized. In this case, a spotter of an ink jet system or an electrostatic system is preferably used in order to prevent the surface of the conductor from being damaged. Moreover, it is also possible to directly synthesize the nucleic acid on the electrode surface.

Figure 2:
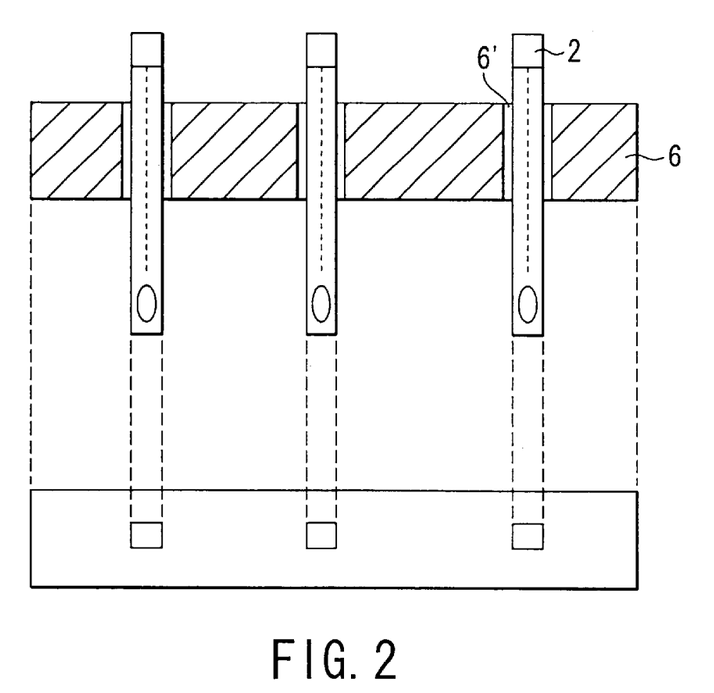
FIG. 2 is a diagram showing one example of a holder of a nucleic acid immobilized electrode.

With use of a plurality of nucleic acid immobilized electrodes, a holder 6 for holding the nucleic acid immobilized electrode 2 as shown in FIG. 2 may be used so that the electrode can be held. An insertion hole 6' for holding the nucleic acid immobilized electrode 2 is disposed in the holder 6.

The insertion hole 6' is preferably formed at a pitch of 36 mm (3×2), 18 mm (6×4), 9 mm (12×8), 4.5 mm (24×16), or 2.25 (48×32) mm at which the held nucleic acid immobilized electrode 2 can be inserted into the commercially available micro titer plate having 24, 48, 96, 384, or 1536 holes. In FIG. 2, a diameter of the insertion hole 6' is shown in an exaggerated manner for convenience of description.

As not shown, a connector is used in order to extract an electric signal from a plurality of nucleic acid immobilized electrodes 2. A type of the connector is not particularly limited. However, for example, in the present embodiment, the connector is formed at a pitch of 36 mm (3×2), 18 mm (6×4), 9 mm (12×8), 4.5 mm (24×16), or 2.25 (48×32) mm at which the connector can be inserted into the commercially available micro titer plate having 24, 48, 96, 384, or 1536 holes.

As a plurality of bottomed vessels 1, it is possible to use a vessel for general use in immunity examination, and the like, in which the electrode is formed in the micro titer plate having 24, 48, 96, 384, or 1536 holes with a plurality of bottomed vessels integrated therein. Such an electrode is a counter electrode 3 opposite the nucleic acid immobilized electrode 3. For the counter electrode 3, a plurality of electrodes can separately be formed for the respective bottomed vessels 1, and one electrode common with the respective vessels 1 can also be disposed in the bottom surface. When a plurality of counter electrodes 3 are disposed on the bottom surface of the micro titer plate integrated with the plurality of bottomed vessels 1, it is also possible to use the matrix system used in the liquid crystal display. Furthermore, the active matrix system using the MOSFET may be used. Additionally, it is also possible to use the MOS image sensor type scanning circuit.

The counter electrode 3 to be disposed in the bottom surface or the side surface of the bottomed vessel 1 preferably has a structure integrated with the bottomed vessel 1, but may have a structure which can be separated from the bottom surface or the side surface of the bottomed vessel. Also in this case, it is possible to form a plurality of counter electrodes 3. The three-electrodes system including the reference electrode in addition to the counter electrode 3 can also be constituted in a similar manner. An ion transmission film in which an electron can move may be disposed between the bottomed vessel 1 and the counter electrode 3.

A material of the counter electrode 3 (and the reference electrode) is not particularly limited, and it is possible to use gold, an alloy of gold, single metals such as silver, platinum, mercury, nickel, palladium, silicon, germanium, gallium, and tungsten, an alloy of these metals, carbons such as graphite and glassy carbon, and an oxide or a compound of these components.

The electrode can be prepared with respect to the bottomed vessel 1 by plating, printing, sputtering, vapor deposition, and the like. With the vapor deposition, the electrode film can be formed by the resistance heating method, high-frequency heating method, and electron beam heating method. Moreover, with the sputtering, the electrode film can be formed by the direct-current bipolar sputtering, bias sputtering, asymmetric alternating-current sputtering, getter sputtering, or high-frequency sputtering.

Moreover, when the reference electrode is formed, silver/silver chloride may also be applied.

These counter electrode 3 and reference electrode can also be formed on hydrophobic films such as a cellulose nitrate film and a nylon film, or through the films. In this case, filtering is possible similarly as a usually used micro plate with a filter attached thereto.

A process of detecting a nucleic acid with use of the nucleic acid detection apparatus shown in FIG. 1 will be described hereinafter.

First, the condition of a time at which the nucleic acid probe is immobilized onto the conductor in order to prepare the nucleic acid immobilized electrode will first be described. Here, an example in which the conductor is gold will be described.

The conductor formed of gold is cleaned with deionized water, and subsequently subjected to an activation treatment. A 0.1 to 10 mol/L sulfuric acid solution is used for activation. A potential is scanned in a range of −0.5 to 2V (vsAg/AgCl) and a range of 1 v/s to 100000 v/s in the solution. Thereby, the electrode surface is activated so that the probe can be immobilized.

The thiol group is introduced beforehand in terminal 5' or 3' of the nucleic acid probe for use in immobilization. The thiolated nucleic acid probe is solved in a solution of a reducing agent such as DTT immediately before the immobilization, and DTT is removed by gel filtration, extraction operation by ethyl acetate, or the like immediately before use.

The immobilization is extremely simple. A probe DNA is solved in a buffer solution within a range of pH 5 to 10 in a range of an ion strength of 0.01 to 5 in order to obtain a range of 1 ng/ml to 1 mg/mL, and the electrode is soaked in the solution immediately after activated. An immobilization reaction is carried out in a range of 4 to 100° C. for ten minutes to about overnight.

After the immobilization of the nucleic acid probe, the electrode is stored on a condition that a nucleic acid decomposition enzyme (nuclease) does not exist, and is shielded if possible. Additionally, for a short period, the electrode may be stored in a wet state. A composition of a stock liquid is preferably a composition of a liquid for performing the hybridization reaction, or a Tris-EDTA buffer solution or the deionized water. Furthermore, the storage temperature is not more than 4° C., and is preferably −20° C. Additionally, when the electrode with the nucleic acid probe immobilized thereto is stored for a long period, the electrode is preferably stored in a dry state. A method of setting the dry state is not particularly limited, and freeze drying, air drying, or the like may be carried out. A gas phase is not particularly limited, and an inactive gas such as argon, nitrogen, dry air, or vacuum state is preferable.

The subject substance (sample) is not particularly limited. It is possible to use, for example, blood, serum, leukocyte, urine, feces, semen, salivary juice, tissue, cultivated cell, phlegm, food, soil, drainage, waste water, air, and the like. Particularly a nucleic acid component extracted from the substance is preferably used as the subject substance. As a method of extracting the nucleic acid component, it is possible to use a liquid—liquid extraction method such as a phenol-chloroform method, or a solid-liquid extraction method in which a carrier is used. Moreover, it is also possible to utilize a marketed nucleic acid extraction method QIAamp (manufactured by QIAGEN Co.), Sumi test (manufactured by Sumitomo Metal Industries, Ltd.), and the like.

Figure 3:
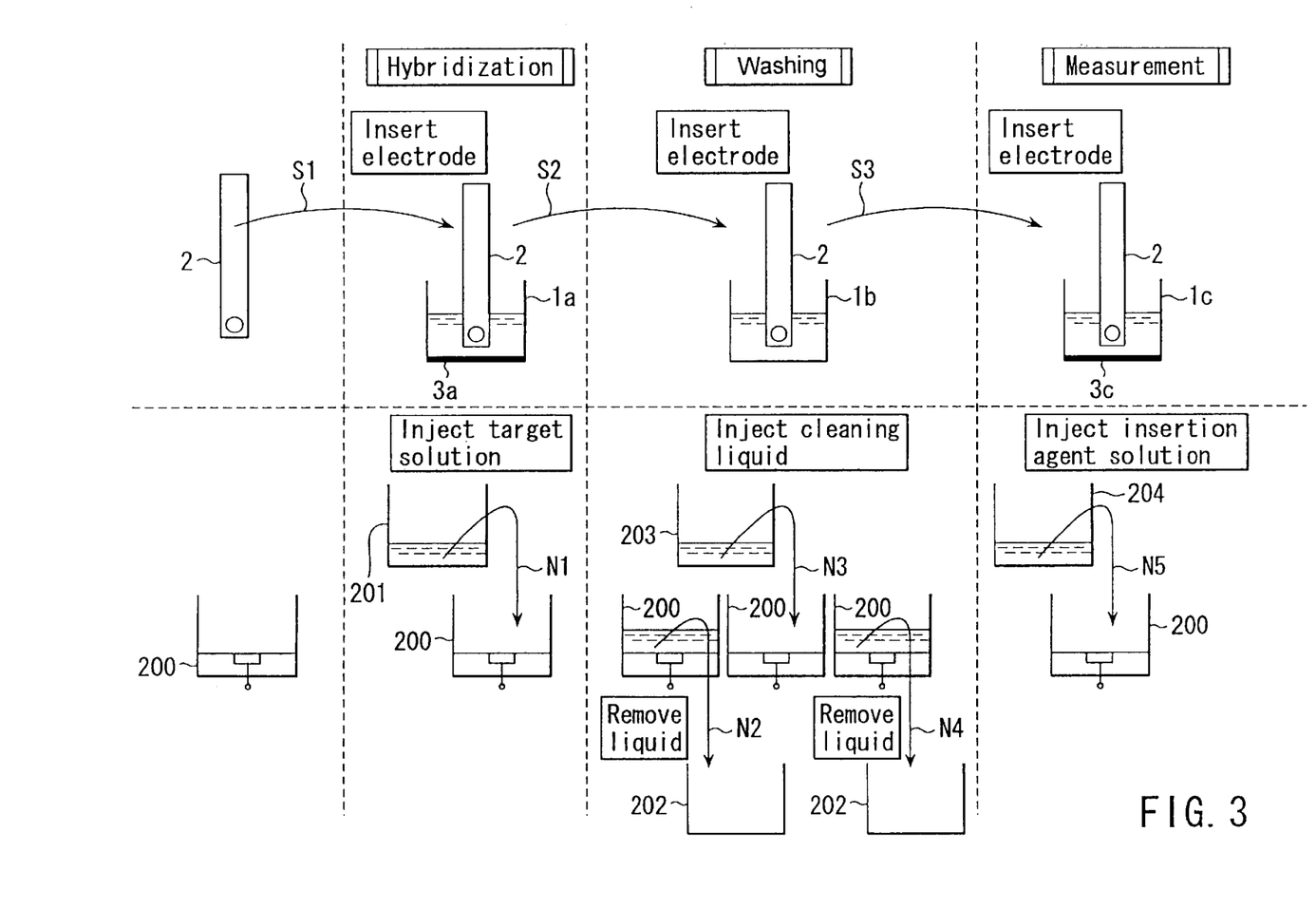
FIG. 3 is a diagram showing a nucleic acid detection process together with a comparative example.

FIG. 3 is a diagram showing the nucleic acid detection process of this embodiment and a comparative example thereof. The nucleic acid detection process according to this embodiment employs the nucleic acid immobilized electrode 2 having a stick-like shape as shown in FIG. 1. The nucleic acid probe 5 is fixed to the nucleic acid immobilized electrode 2. The counter electrode 3 is disposed on the bottom surface or side surface of the bottomed vessel 1 to which the nucleic acid immobilized electrode 2 is inserted. A voltage is applied between the electric circuit 4 between the nucleic acid immobilized electrode 2 and the counter electrode 3. In this embodiment, a plurality of bottomed vessels are used, and different bottomed vessels are used at least between a hybridization reaction process and a nucleic acid measurement process. For example, in this embodiment, three bottomed vessels 1a to 1c are used. A counter electrode 3a is disposed on the bottom surface of the bottomed electrode 1a. The bottomed vessel 1b is designed to clean the nucleic acid immobilized electrode 2, and therefore no counter electrode is provided. As in the bottomed vessel 1a, a counter electrode 3c is provided on the bottom surface of the counter electrode 1c.

In the meantime, in the nucleic acid detection process of the comparative example, only one vessel 200 in which an electrode to which a nucleic acid probe is immobilized, is provided on the bottom surface. Here, a vessel 201 for dispensing a reaction solution to the vessel, a vessel 202 for discarding an unnecessary portion of the solution, separated from the vessel 200, a vessel 203 for dispensing a washing solution to the vessel 200 and a vessel 204 for dispensing a nucleic acid binding reagent solution to the vessel 200 are used.

In order to detect a particular nucleic acid, it is necessary to carry out a process for denaturing a double stranded nucleic acid in the subject substance into single stranded nucleic acid. Then, a hybridization reaction between the nucleic acid probe and the single stranded nucleic acid. This process is common to the nucleic detection process of the present invention and the process of the comparative example.

First, a reaction solution containing the subject substance containing double stranded nucleic acid is injected to the bottomed vessel 1a. Then, the double stranded nucleic acid into the single stranded nucleic acid. Then, the nucleic acid immobilized electrode 2 is moved to a position of the bottomed vessel 1a as shown in FIG. 3 (Step S1).

Figure 4:
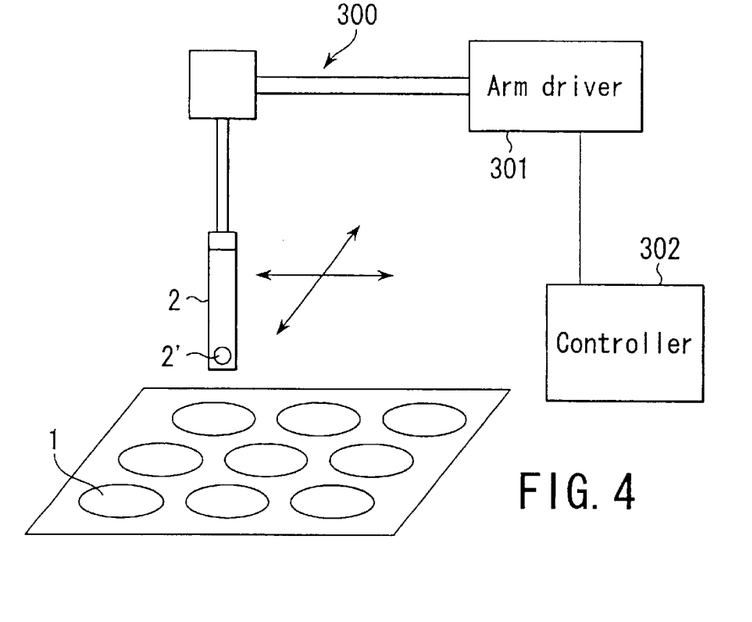
FIG. 4 is a diagram showing a constitution example of a movement control mechanism of the nucleic acid immobilized electrode.

FIG. 4 is a diagram showing an example of the structure of a movement control mechanism for the nucleic acid immobilized electrode. The movement control mechanism shown in this figure includes an arm portion 300 for holding the nucleic acid immobilized electrode 2, an arm drive portion 301 for driving the arm portion 300 in a direction indicated by an arrow in this figure, and a control portion 302 for controlling the driving of the arm drive portion 300 by the arm drive portion 301. In compliance with a control instruction from the control portion 302, the arm drive portion 301 drives the arm portion 300 so as to move the nucleic acid immobilized electrode 2 to a predetermined position on the bottomed vessel 1. Then, the arm drive portion 301 drives the arm portion 300 so as to move the nucleic acid immobilized electrode 2 in a downward direction until the exposed portion 2' of the conductor of the nucleic acid immobilized electrode 2 is immersed into the solution in the bottomed vessel 1.

The hybridization reaction process takes place in the following manner. That is, the reaction solution containing the subject substance is injected into the bottomed vessel 1a and the subject substance is added thereto. Then, the nucleic acid immobilized electrode 2 is inserted to the bottomed vessel 1a so that a hybridization reaction occurs between the nucleic acid component of the subject substance and the exposed portion 2' of the nucleic acid immobilized electrode 2.

The process so far will concretely be described hereinafter.

As the reaction solution, the buffer solution having a range of ion strength of 0.01 to 5 and a range of pH 5 to 10 is preferable. It is possible to add dextran sulfate as a hybridization promoter, salmon sperm DNA, calf thymus DNA, EDTA, surfactant, Dextan sulphate, Form amide, BSA (Bovine Serum albumin), PVP (polyvinyl pyrrolidone), or the like into the solution.

Subsequently, the subject substance is further injected into the reaction solution, and the double stranded nucleic acid is thermally denatured into single stranded type by heating it at 90° C. or more. The nucleic acid immobilized electrode can be inserted immediately after the denaturation, or after quenching at 0° C.

A reaction speed can also be raised by operations such as stirring and shaking during the hybridization reaction. The reaction temperature is set to a range of 10° C. to 90° C., and reaction time is at least one minute or more, and is preferably about overnight.

It is possible to electrochemically control the hybridization reaction subsequent to the thermal denaturation. The voltage is applied between the electrode 3a disposed on the side surface or the bottom surface of the bottomed vessel 1a, and the nucleic acid immobilized electrode 2 by the electric circuit 4 so that the surface of the electrode 2' has a plus voltage. Then, the minus charged nucleic acid is condensed on the electrode 2' surface and the reaction is promoted. Additionally, when a minus voltage is applied to the electrode surface 2', the nonspecific coupling can be removed.

When the plus voltage is applied to the electrode 2, the conventional reaction time of several hours to several days is shortened to several minutes. In this case, the voltage is swept at a constant speed, a pulse is applied, or a constant voltage is applied. The electric circuit 4 includes a potentiostat, digital multimeter, and function generator, and the circuit applies the potential under current or voltage control.

After the hybridization reaction, the electrode is extracted and cleaned on this embodiment.

The movement control mechanism moves the nucleic acid immobilized electrode 2 to a position of the bottomed vessel 1b, so as to immerse it in the washing solution within the vessel 1b. In the washing, the buffer solution having an ion strength in a range of 0.01 to 5 and a pH in a range of 5 to 10 is used for washing the electrode. It should be noted that this washing process is not essential to the invention.

After the washing, the movement control mechanism 5 moves the nucleic acid immobilized electrode 2 to a position of the bottomed vessel 1b, so as to immerse it in the washing solution within the vessel 1b. In the measurement process which follows the washing process, the nucleic acid binding reagents is allowed to act and is selectively coupled to a double stranded portion formed in the surface of the electrode 2', and the electrochemical signal is measured. For the electrochemical signal, a redox current change generated between the nucleic acid immobilized electrode 2 and the counter electrode 3c, redox potential change, electric capacity change, resistance change, or electrochemical emission change can be used as an indication. An effect of the signal change is promoted also by using the nucleic acid binding reagents, that is, a substance particularly coupled to the double stranded nucleic acid.

The double stranded nucleic acid binding reagents (such as interealator) for use herein is not particularly limited. It is possible to use ruthenium called metallo-intercalator, metal complexes such as cobalt and iron, organic compounds such as Hoechst 33258, acridine orange, ethidium bromide, bis-intercalator, and tris-intercalator, and biopolymers such as antibody and enzyme. Moreover, it is also possible to detect nucleic acid in sandwich hybridization in which a second nucleic acid probe labeled with the metal complexes such as ferrocene is used.

The nucleic acid binding reagents such as Hoechst 33258, acridine orange, quinatarine, donomicine, metallo-intercalator, bis-intercalator such as bis-acridine, tris-intercalator, and polyintercalator are particularly desirable.

A concentration of the nucleic acid binding reagent differs with a type, and the reagent is generally used in a range of 1 ng/ml to 1 mg/ml. In this case, the buffer solution having a range of pH 5 to 10 is used in a range of ion strength of 0.001 to 5.

After the electrode 2' is reacted with the nucleic acid binding reagent, the electrochemical measurement is performed. In the measurement, a voltage having a potential at which the nucleic acid binding reagent is electrochemically reacted or more potential is applied to the electrode 2' by the electric circuit 4, and a reaction current value resulting from the nucleic acid binding reagent is measured. In this case, the voltage is swept at a constant speed, the pulse is applied, or the constant voltage is applied.

The voltage is applied between the electrode 3c disposed on the side surface or the bottom surface of the bottomed vessel 1c, and the exposed portion 2' of the conductor of the nucleic acid immobilized electrode 2.

As a result, the concentration of a target gene can be calculated from a working curve based on the current value obtained from the nucleic acid binding reagent.

Next, the nucleic acid detection process of the comparative example will now be described.

First, the reaction solution is dispensed to the bottomed vessel 200 in which the nucleic acid immobilized electrode is disposed on the bottom surface thereof, so that the above-described denaturation and hybridization reaction occur (step N1). The denaturation and hybridization reaction themselves are similar to the above-described processes of this embodiment. Then, the reaction solution used in the hybridization reaction is removed from the bottomed vessel 200, and discarded to the vessel 202 (step N2). Next, the washing solution is dispensed to the bottomed vessel 200 from which the reaction solution has been removed (step N3). Thus, after washing the bottomed vessel 200, the washing solution is removed from the bottomed vessel 200 and discarded to the vessel 202 (step N4).

Then, the nucleic acid binding reagent solution is dispensed from the vessel 204 to the bottomed vessel 200 from which the washing solution has been removed, and thus the measurement process is executed (step N5).

As is clear from the explanation, it is necessary in the nucleic acid detection process of the comparative example to repeatedly carry out the dispensing of the solution and discarding of the solution since the bottomed vessel which includes the nucleic acid immobilized electrode on its bottom surface is employed here.

By contrast, in the nucleic acid detection process of the present invention, a plurality of bottomed vessels each equipped with a counter electrode on its bottom surface, are used, and the nucleic acid immobilized electrode 2 is moved to a respective one of the bottomed vessels. In other words, the vessel for the hybridization reaction and the vessel used for the measurement are separated from each other.

Therefore, according to the present invention, the solution discarding operation of the comparative example is not necessary, and thus the nucleic acid detection process can be facilitated. Such a structure is effective in the case where a great number of subject substances are examined.

Further, since the vessel for the hybridization reaction and the vessel used for the measurement are separated from each other, it is possible to avoid a non-specific binding resulted during the hybridization process, from remaining in the measurement process. Such a non-specific bonds may cause an undesired current, which creates noise in a measurement result. Therefore, the prevention of such a non-specific binding can contribute to noise reduction in the measurement result.

EXAMPLE 1

Nucleic Acid Immobilized Electrode

Figure 5:
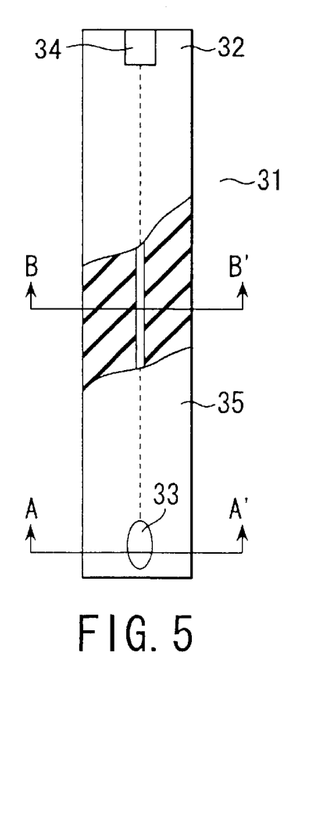
FIG. 5 is a diagram showing one example of the nucleic acid immobilized electrode according to Example 1.

FIG. 5 is a diagram showing one example of the nucleic acid immobilized electrode for the nucleic acid detection apparatus. A nucleic acid immobilized electrode 31 was prepared by laminating thin films of titanium (500 angstroms) and gold (2000 angstroms) on a glass substrate 32 having a thickness of 0.8 mm in order of the glass substrate, titanium, and gold by sputtering, and coating the gold surface with a resist 35 excluding a nucleic acid probe immobilized portion 33 (circular region with a diameter of 0.5 mm) and terminal portion 34.

That is, the nucleic acid probe immobilized portion 33 and terminal portion 34 are connected to each other on a back-surface side of the resist 35. Moreover, the thiolated nucleic acid probe is immobilized in the nucleic acid probe immobilized portion 33 with coupling of thiol/gold. An outer shape of the present electrode is set to have a width of 1.5 mm so that the electrode is inserted in the micro titer plate having 384 holes. Moreover, a length is 5 cm.

Figure 6:
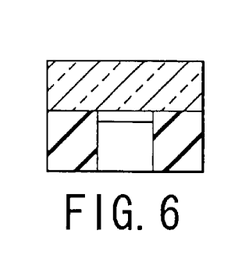
FIG. 6 is a sectional view taken along line A–A' in the nucleic acid immobilized electrode shown in FIG. 5.
Figure 7:
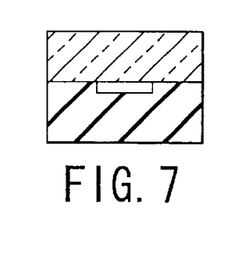
FIG. 7 is a sectional view taken along line B–B' in the nucleic acid immobilized electrode shown in FIG. 5.

FIG. 6 is a diagram showing a cross sectional view of the nucleic acid probe immobilized electrode 31 taken along the line A–A', and FIG. 6 is a diagram showing a cross sectional view of the nucleic acid probe immobilized electrode 31 taken along the line B–B'.

EXAMPLE 2

Nucleic Acid Immobilized Electrode

Figure 8:
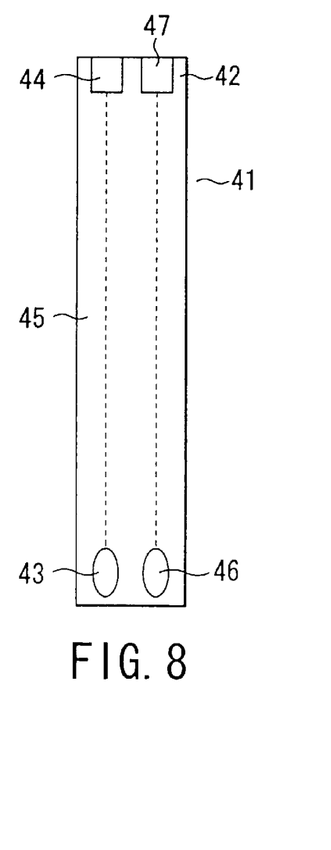
FIG. 8 is a diagram showing one example of a nucleic acid immobilized electrode structure including a counter electrode or reference electrode according to Example 2.

FIG. 8 is a diagram showing one example of an electrode structure 41 in which the nucleic acid immobilized electrode and reference electrode for the nucleic acid detection apparatus are integrated. The electrode structure 41 was prepared as follows. First, titanium (500 angstroms) and gold (2000 angstroms) were laminated on a glass substrate 42 having a thickness of 0.8 mm in order of the glass substrate, titanium, and gold by sputtering, and were formed in two lines along a longitudinal direction of the substrate. Furthermore, with respect to the laminate of titanium and gold, the gold surface of one line was coated with a resist 45 excluding a nucleic acid probe immobilized portion 43 (circular region with a diameter of 0.5 mm) and terminal portion 44. The gold surface of another line was coated with the resist 45 excluding a reference electrode (circular region with a diameter of 0.5 mm) portion 46 in which silver/silver chloride was formed and terminal portion 47. The reference electrode portion 46 was subjected to electrolysis in a silver/silver chloride solution, and deposited and formed on a gold electrode surface. The thiolated nucleic acid probe was immobilized in the probe immobilized portion 43 with coupling of thiol/gold. For the outer shape of the present electrode structure, a width is set to 3 mm so that the structure can be fit in the micro plate having 96 holes. Moreover, a length is 10 cm.

EXAMPLE 3

Holder of Nucleic Acid Immobilized Electrode

Figure 9:
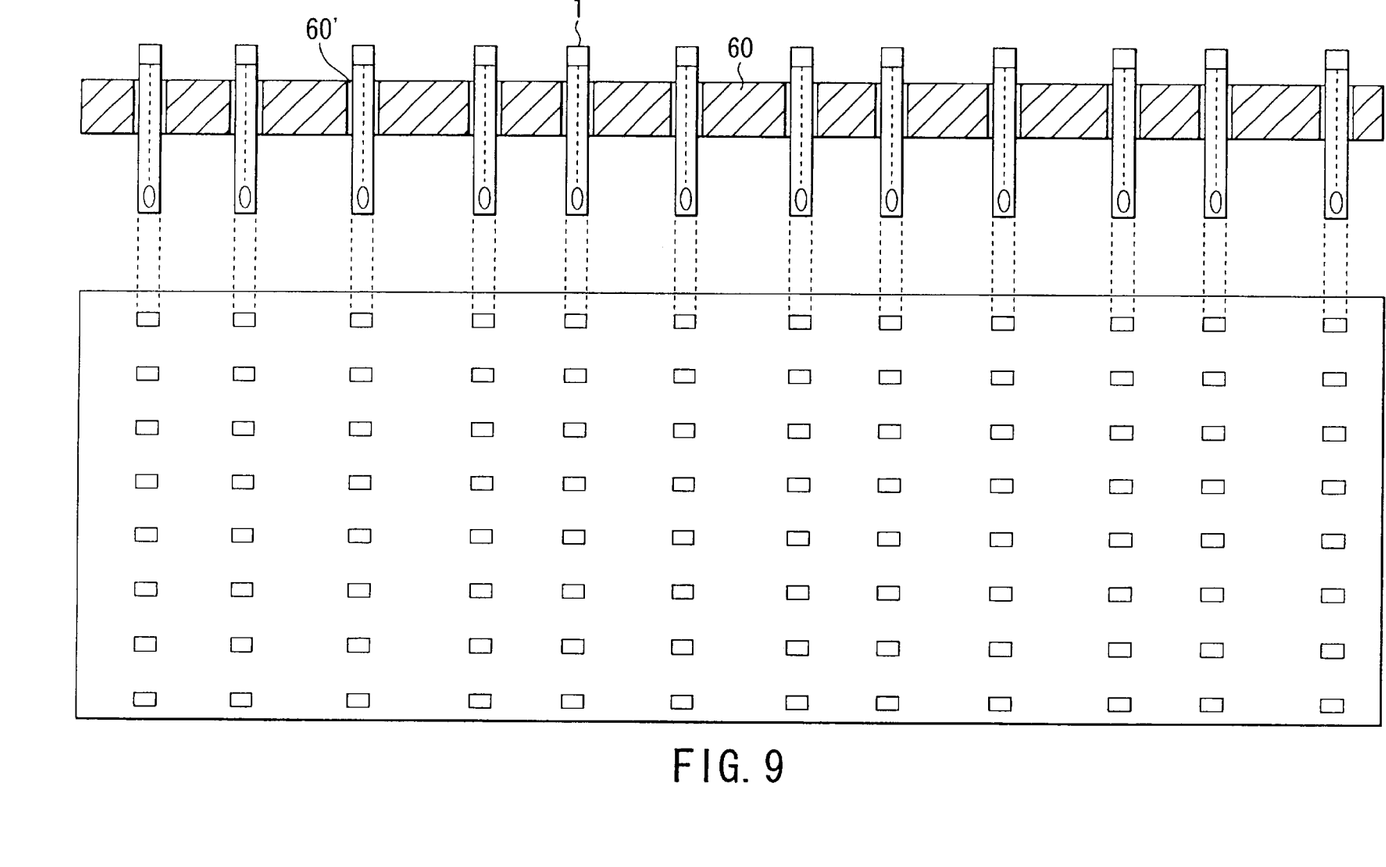
FIG. 9 is a diagram showing one example of the holder of the nucleic acid immobilized electrode according to Example 3.

FIG. 9 is a sectional view showing one example of the holder of the nucleic acid immobilized electrode. In a holder 60 for supporting nucleic acid immobilized electrodes 2, insertion holes 60' are arranged at a pitch of 6 mm in an array of 12×8 holes, and the nucleic acid immobilized electrodes 2 are disposed in the insertion holes 60', so that the plurality of nucleic acid immobilized electrodes 2 can be inserted once in the micro titer plate having 96 holes.

EXAMPLE 4

Electrode Integrated Type Micro Titer Plate

Figure 10:
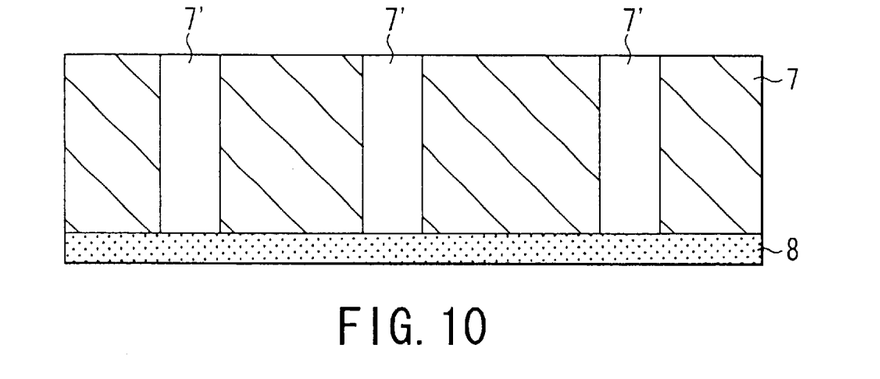
FIG. 10 is a diagram showing one example of an electrode integrated type micro titer plate according to Example 4.

FIG. 10 is a sectional view showing one example of an electrode integrated type micro titer plate as a vessel for nucleic acid detection. A plurality of bottomed vessels 7' are disposed in a micro titer plate 7. A carbon film electrode (counter electrode) 8 is attached to a bottom surface of each bottomed vessel 7'. When a liquid is injected into the bottomed vessel 7', the liquid directly contacts the carbon film electrode 8, or is held in the bottomed vessel 7'.

EXAMPLE 5

Electrode Integrated Type Micro Titer Plate

Figure 11:
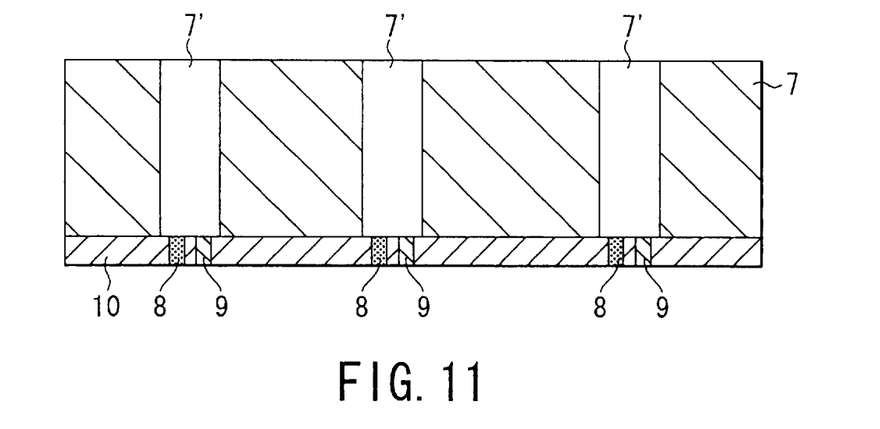
FIG. 11 is a diagram showing one example of the electrode integrated type micro titer plate according to Example 5.

FIG. 11 is a sectional view showing one example of the electrode integrated type micro titer plate as the vessel for nucleic acid detection. The plurality of bottomed vessels 7' are disposed in the micro titer plate 7. A nitrocellulose film 10 to which the carbon film electrode 8 and a carbon film electrode 9 with silver/silver chloride formed therein are attached is disposed in the bottom surface of each bottomed vessel 7', and the liquid is held in the vessel. Reference numeral 8 denotes the counter electrode, and 9 denotes the reference electrode. The liquid is held in the vessel. Filtering by suction is possible in accordance with a use method.

EXAMPLE 6

Electrode Integrated Type Micro Titer Plate

Figure 12:
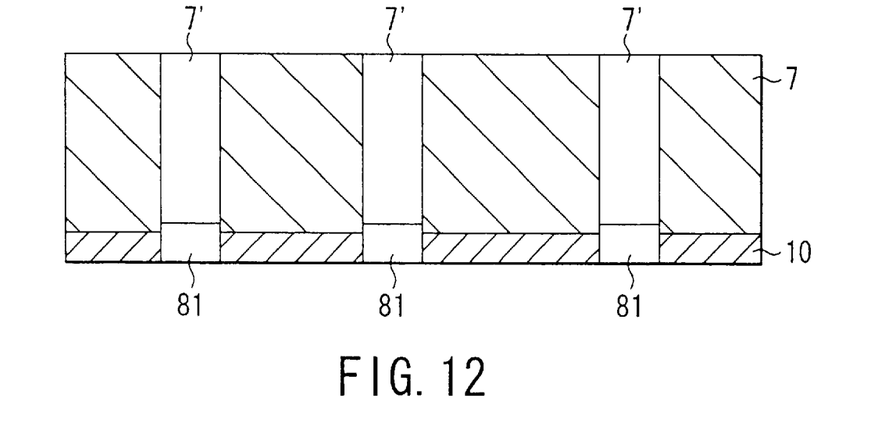
FIG. 12 is a diagram showing one example of the electrode integrated type micro titer plate according to Example 6.

FIG. 12 is a sectional view showing one example of the electrode integrated type micro titer plate as the vessel for nucleic acid detection. The plurality of bottomed vessels 7' are disposed in the micro titer plate 7. The nitrocellulose film 10 in which respective gold electrodes (counter electrodes) 81 are formed is attached to the bottom surface of each bottomed vessel 7'. When the liquid is injected into the bottomed vessel 7', the liquid contacts the gold electrode 81, or is held in the bottomed vessel 7'. The filtering by suction is possible in accordance with the use method.

EXAMPLE 7

Electrode Separated Type Micro Titer Plate

Figure 13:
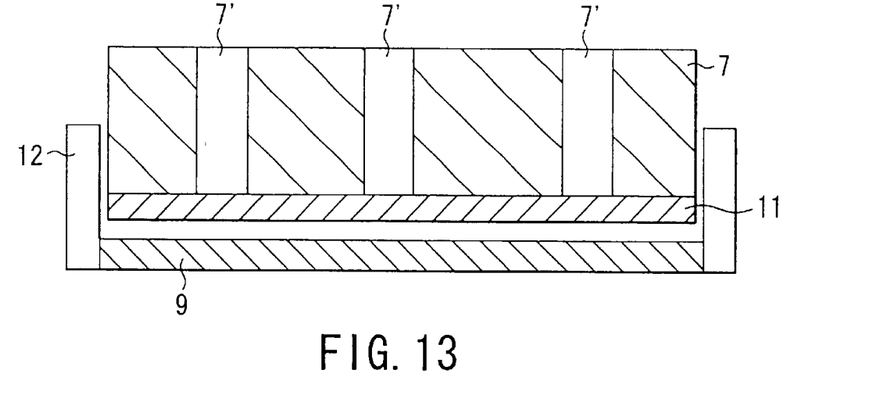
FIG. 13 is a diagram showing one example of an electrode separated type micro titer plate according to Example 7.

FIG. 13 is a sectional view showing one example of an electrode separated type micro titer plate as the vessel for nucleic acid detection. The plurality of bottomed vessels 7' are disposed in the micro titer plate 7. A hydrophobic filter 11 in which ion can move is attached to the bottom surface of the bottomed vessel 7', and the liquid can be held in the vessel. A vessel 12 to which a carbon film electrode (counter electrode) 91 is attached is disposed under the filter, and the voltage is applied to the constitution via the filter 11.

EXAMPLE 8

Electrode Separated Type Micro Titer Plate

Figure 14:
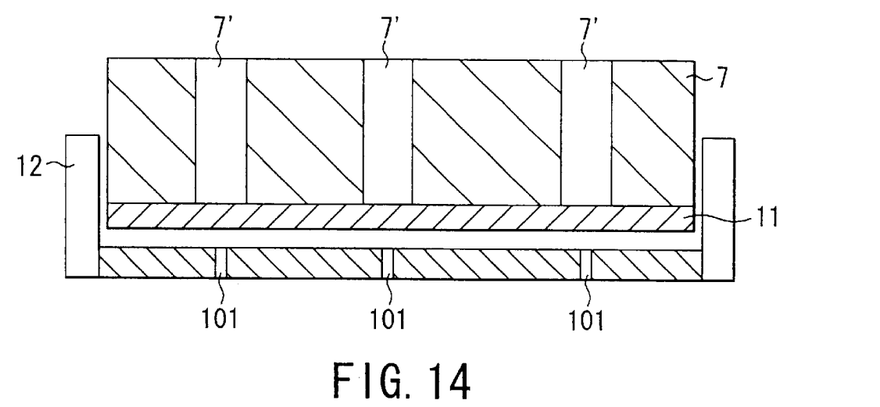
FIG. 14 is a diagram showing one example of the electrode separated type micro titer plate according to Example 8.

FIG. 14 is a diagram showing one example of the electrode separated type micro titer plate as the vessel for nucleic acid detection. The plurality of bottomed vessels 7' are disposed in the micro titer plate 7. The hydrophobic filter 11 in which ion can move is attached to the bottom surface of the bottomed vessel 7', and the liquid can be held in the vessel. The vessel 12 to which a carbon film electrode (counter electrode) 101 for each bottomed vessel 7' is attached is disposed under the filter, and these electrodes are connected to an external power source via a wiring having a matrix structure.

EXAMPLE 9

Electrode Separated Type Micro Titer Plate

Figure 15:
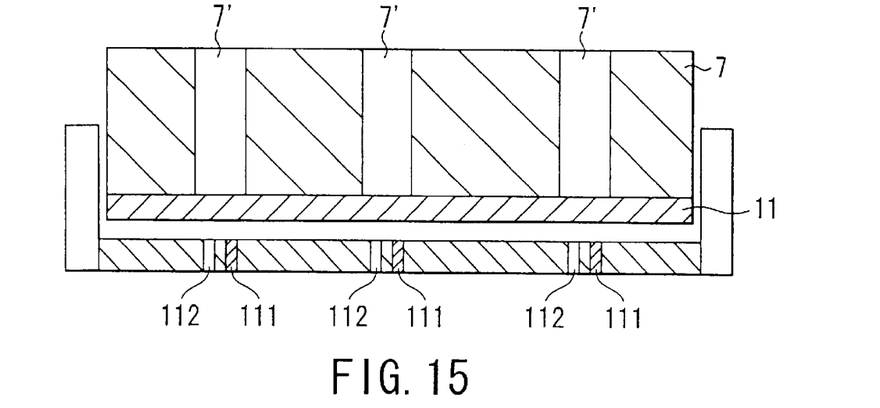
FIG. 15 is a diagram showing one example of the electrode separated type micro titer plate according to Example 9.

FIG. 15 is a diagram showing one example of the electrode separated type micro titer plate as the vessel for nucleic acid detection. The plurality of bottomed vessels 7' are disposed in the micro titer plate 7. The hydrophobic filter 11 in which ion can move is attached to the bottom surface of the micro titer plate 7, and the liquid can be held in the vessel. Carbon film electrodes (counter electrodes) 112, and carbon film electrodes (reference electrodes) 111 with silver/silver chloride formed therein are disposed opposite to the respective bottomed vessels 7' under the filter, and these electrodes are connected to the external power source via the wiring having an active matrix structure.

EXAMPLE 10

Electrode Arrangement of Electrode Separated Type Micro Titer Plate

Figure 16:
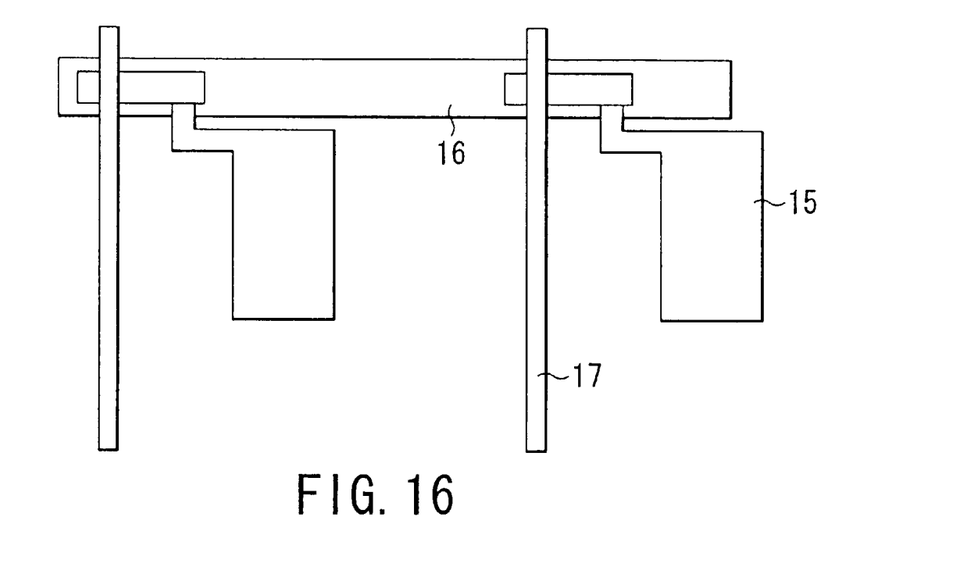
FIG. 16 is a diagram showing one example of an electrode arrangement of the electrode separated type micro titer plate according to Example 10.

FIG. 16 is a diagram schematically showing an electrode wiring for each electrode with use of the electrode separated type micro titer plate according to Example 8. A carbon film electrode 15 (represented as the carbon film electrode 101 in Example 8) is connected to a gate line 16 and source line 17, and the voltage from the power source is applied to the structure via the source line 17. Switching is performed by turning ON/OFF the gate line.

EXAMPLE 11

Electrode Arrangement of Electrode Separated Type Micro Titer Plate

Figure 17:
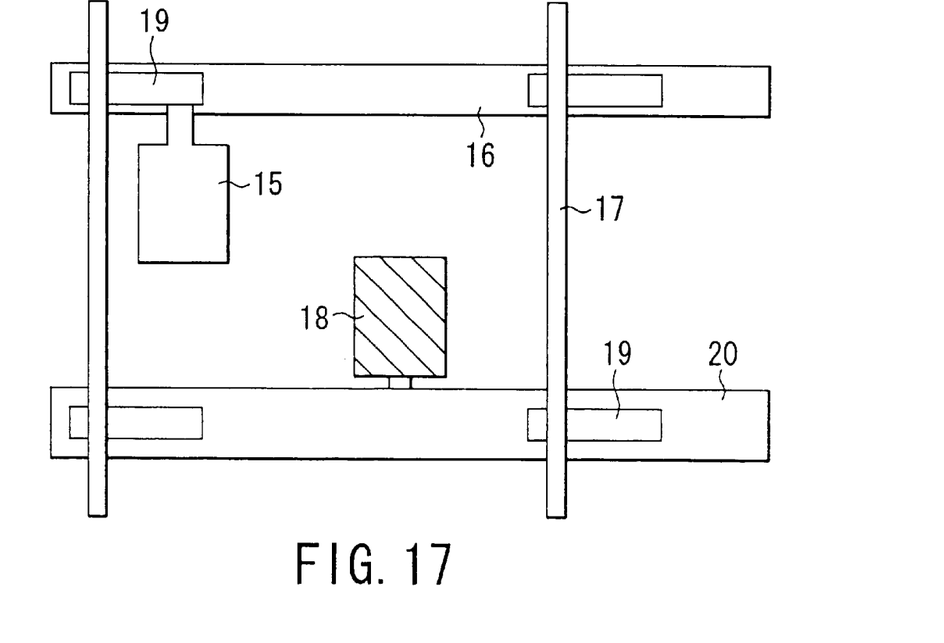
FIG. 17 is a diagram showing one example of the electrode arrangement of the electrode separated type micro titer plate according to Example 11.

FIG. 17 is a diagram schematically showing the electrode wiring for each electrode with use of the electrode separated type micro titer plate according to Example 9. The carbon film electrode 15 (represented as the carbon film electrode 112 in Example 9) acts as the counter electrode. The carbon film electrode 15 is connected to the gate line 16 and source line 17, and the voltage from the power source is applied to the structure via the source line 17. The switching is performed by turning ON/OFF a TFT 19 connected to the gate line 16. Moreover, a silver chloride/silver electrode 18 (represented as the carbon film electrode 111 with silver/silver chloride formed therein in Example 9) acts as the reference electrode. The silver/silver chloride electrode 18 is connected to a gate line 20 and source line 17, and the voltage is applied to the structure via the source line. The switching is performed by turning ON/OFF the TFT 19 connected to the gate line 20.

EXAMPLE 12

Detection Apparatus Using Electrode Integrated Type Micro Titer Plate

Figure 18:
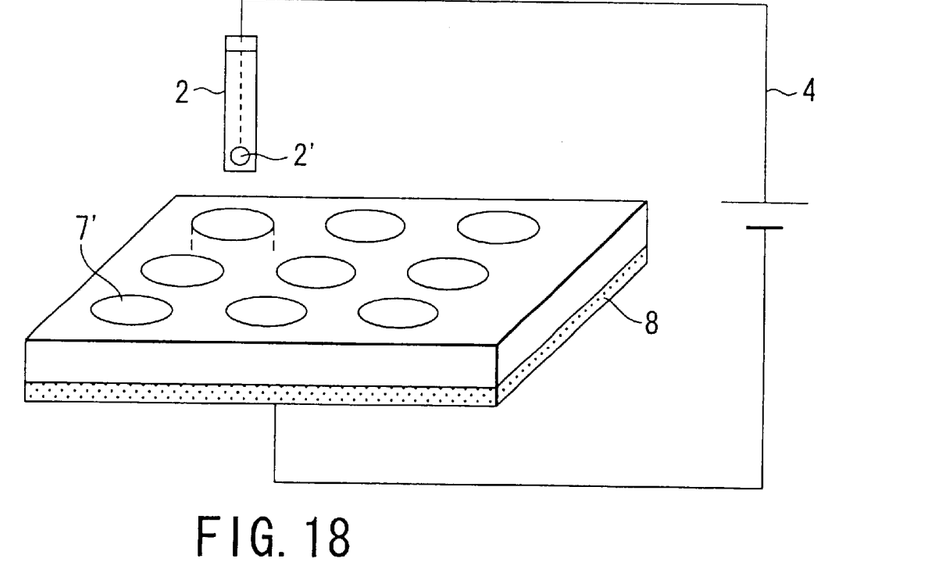
FIG. 18 is a diagram showing one example of a nucleic acid detection apparatus using the electrode integrated type micro titer plate according to Example 12.

FIG. 18 shows a nucleic acid detection apparatus in which the electrode integrated type micro titer plate of Example 4 and the nucleic acid immobilized electrode of Example 1 are used. The apparatus includes: the nucleic acid immobilized electrode 2; a 96-holes micro titer plate including the plurality of bottomed vessels 7' separated from one another and counter electrodes 8 disposed in the bottom surfaces of the bottomed vessels 7'; and means (power source) 4 for applying the voltage between the nucleic acid immobilized electrode 2 and the counter electrode 8.

The subject substance containing the gene extracted from blood is inoculated into the bottomed vessel 7' of the micro titer plate, and the nucleic acid immobilized electrode 2 is inserted. The hybridization reaction can be promoted by applying the voltage of 0.5V between the nucleic acid immobilized electrode 2 and the counter electrode 8. The reaction ended in about five minutes. Subsequently, the nucleic acid binding reagent of Hoechst 33258 was added, and a current during application of the voltage was measured. The voltage of 0.6V was applied between the electrodes 2 and 8 for the current measurement of Hoechst 33258, and it was possible to simultaneously detect the genes with respect to 96 samples.

EXAMPLE 13

Detection Apparatus Using Electrode Separated Type Micro Titer Plate

Figure 19:
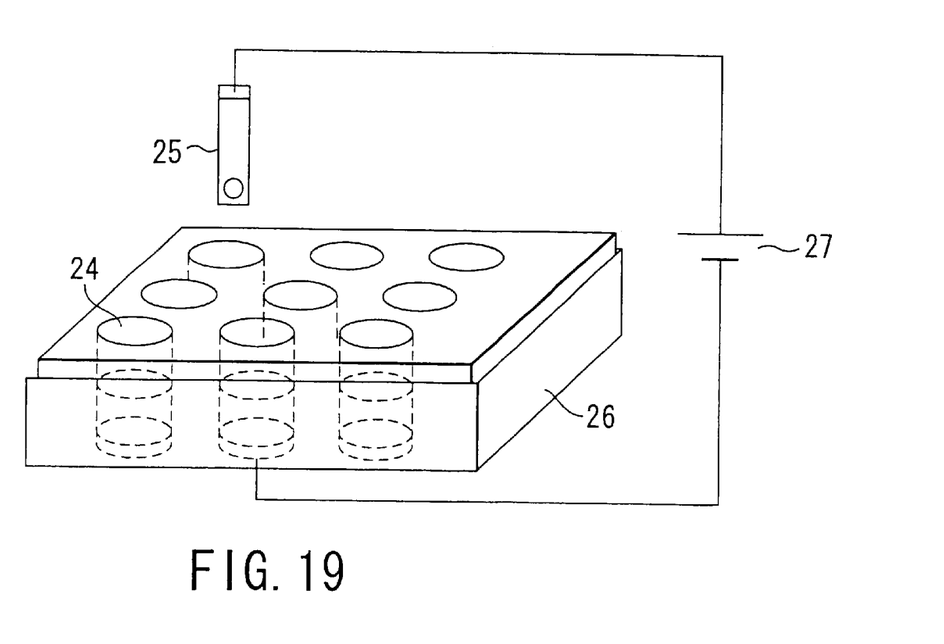
FIG. 19 is a diagram showing one example of the nucleic acid detection apparatus using the electrode separated type micro titer plate according to Example 13.

FIG. 19 shows a nucleic acid detection apparatus in which the electrode separated type micro titer plate of Example 7 and the nucleic acid immobilized electrode of Example 1 are used. The apparatus includes: a nucleic acid immobilized electrode 25; the 96-holes micro titer plate including a plurality of bottomed vessels 24 separated from one another and vessels including counter electrodes 26 positioned in the bottom surfaces of the bottomed vessels 24; and means (power source) 27 for applying the voltage between the nucleic acid immobilized electrode 25 and the counter electrode 26.

The subject substance containing the gene extracted from blood is inoculated into the bottomed vessel 24 of the 96-holes micro titer plate, and the nucleic acid immobilized electrode 25 is inserted. The hybridization reaction can be promoted by applying the voltage of 0.5V between the electrode 25 and the counter electrode 26. The reaction ended in about five minutes. Subsequently, the nucleic acid binding reagent of Hoechst 33258 was added, and the current during application of the voltage was measured. The voltage of 0.6V was applied between the electrode 25 and the counter electrode 26 for the current measurement of Hoechst 33258, and it was possible to simultaneously detect the genes with respect to 96 samples.

The nucleic acid detected by the nucleic acid detection apparatus of the present invention is not particularly limited. For example, the nucleic acid can be used to detect: virus infectious diseases of a hepatitis virus (A, B, C, D, E, F, G type), HIV, influenza virus, herpes group virus, adenovirus, human polyoma virus, human papilloma virus, human parvovirus, mumps virus, human rotavirus, enterovirus, Japanese encephalitis virus, dengue virus, rubella virus, HTLV, and the like; bacterial infectious diseases of yellow staphylococcus, hemolytic streptococci, enteropathogenic *Escherichia coli, Vibrio parahaemolyticus, Helicobacter pylori,* Campylobacter, cholera vibrio, dysentery bacillus, salmonella, Yersinia, gonococcus, Listeria, leptospira, *Legionella pneumophila,* spirochete, *Mycoplasma pneumoniae,* rickettsia, chlamydia, malaria, amoeba dysenteriae, pathogenic fungus, and the like; parasite; and true fungus.

Moreover, it is possible to examine hereditary diseases, and tumorous diseases such as retinoblastoma, Wilms tumor, familial adenomatous polyposis, hereditary nonpolyposis colon cancer, neurofibromatosis, familial breast cancer, xeroderma pigmentosum, brain tumor, oral cavity cancer, esophagus carcinoma, gastric cancer, colon and rectum carcinoma, liver cancer, pancreas cancer, lung cancer, thyroid gland tumor, mammary gland tumor, urinary organs tumor, male genital organs tumor, female genital organs tumor, skin tumor, bone/soft tissue tumor, leukemia, lymphomatosa, and solid tumor.

Moreover, in addition to medical treatment, the present invention can be applied to all fields requiring gene examination, such as food examination, quarantine, medical supplies examination, forensic medicine, agriculture, stock raising, fishery, and forestry. Furthermore, it is also possible to detect restriction fragment length polymorphism (RFLP), single base polymorphism (SNPs), micro satellite sequence, and the like. Additionally, the present invention can also be used in unknown base sequence analysis. Further, the present invention can be applied to analysis of mRNA chain, cDNA chain and cRNA chain.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of electrochemically detecting presences of nucleic acids each having a particular sequence in a plurality of target nucleic acids, comprising:

preparing first and second vessels, wherein in the second vessel, a solution of a nucleic acid binding reagent is dispensed, and at least the second vessel has a counter electrode on a bottom surface or an inside surface thereof;

inserting the target nucleic acids into the first vessel;

inserting to the first vessel a nucleic acid immobilized electrode having a stick-like-shape, on which multiple electrodes are formed, where multiple nucleic acid probes are immobilized to the multiple electrodes and the multiple electrodes are connected to an electric-circuit;

making a hybridization reaction to occur in the first vessel;

extracting the nucleic acid immobilized electrode from the first vessel and inserting the electrode into the second vessel;

applying a predetermined voltage between the nucleic acid immobilized electrode and the counter electrode so as to measure electrochemical signals generated due to the nucleic acid binding reagent solution; and selecting one of the electrochemical signals by the electric-circuit to determine one of the plurality of target nucleic acids.

2. The method according to claim 1, wherein the electric-circuit comprises an active matrix system including MOSFETs.

3. The method according to claim 1, wherein a hybridization promoter is added for a hybridization reaction.

4. The method according to claim 1, further comprising:
actively denaturing a double stranded nucleic acid in the target nucleic acid into single stranded type.

5. The method according to claim 1, wherein the nucleic acid binding reagent solution acts on coupling between the nucleic acid probes and the target nucleic acids, to generate the electrochemical signals.

6. The method according to claim 3, further comprising:
applying a voltage to the nucleic acid immobilized electrode to promote the hybridization reaction.

7. The method according to claim 1, wherein the first vessel and the second vessel are formed in a micro titer plate.

8. The method according to claim 7, wherein a plurality of the first vessels and a plurality of the second vessels are formed in the micro titer plate.

9. The method according to claim 7, wherein there is only one counter electrode common to said plurality of each of the first vessels and the second vessels.

10. The method according to claim 7, wherein the counter electrode is formed on the bottom surface or the inside surface of each of said plurality of the first vessels and the second vessels.

11. A method of electrochemically detecting presences of nucleic acids each having a particular sequence in a plurality of target nucleic acids, comprising:

preparing first and second vessels, wherein in the second vessel, a solution of a nucleic acid binding reagent is dispensed, and at least the second vessel having a counter electrode on a bottom surface or an inside surface thereof;

inserting the target nucleic acids into the first vessel;

inserting to the first vessel a nucleic acid immobilized electrode having a stick-like shape, on which multiple electrodes are formed, where multiple nucleic acid probes are immobilized to the multiple electrodes and the multiple electrodes are connected to an electric-circuit;

making a hybridization reaction to occur in the first vessel;

extracting the nucleic acid immobilized electrode from the first vessel and inserting the electrode into a washing vessel;

washing the nucleic acid immobilized electrode in the washing vessel;

extracting the nucleic acid immobilized electrode from the washing vessel and inserting the electrode to the second vessel;

applying a predetermined voltage between the nucleic acid immobilized electrode and the counter electrode so as to measure electrochemical signals generated due to the nucleic acid binding reagent solution; and selecting one of the electrochemical signals by the electric-circuit to determine one of the plurality of target nucleic acids.

12. A nucleic acid detection apparatus for electrochemically detecting presences of nucleic acids each having a particular sequence in a plurality of target nucleic acids, comprising:

a nucleic acid immobilized electrode having a stick-like shape, on which multiple electrodes are formed, where multiple nucleic acid probes are immobilized to the multiple electrodes;

a first electric-circuit connected to the multiple electrodes, configured to select one of electrochemical signals to be generated;

a vessel configured to bring the nucleic acid probe and the target nucleic acids into contact with each other;

a counter electrode formed on a bottom surface or inside surface of the vessel; and a second electric-circuit configured to apply a voltage between the nucleic acid immobilized electrode and the counter electrode.

13. A nucleic acid detection vessel comprising:

a nucleic acid immobilized electrode having a stick-like shape, on which multiple electrodes are formed, where multiple nucleic acid probes are immobilized to the multiple electrodes and the multiple electrodes are connected to an electric-circuit;

a vessel body; and a first electrode formed on a bottom surface or inside surface of the vessel body, wherein the first electrode is used as a counter electrode.

14. A nucleic acid detection vessel according to claim 13, further comprising:

a second electrode formed on the bottom surface or inside surface of the vessel body, wherein the second electrode is used as a reference electrode.

* * * * *